US009809928B2

(12) United States Patent
Fish et al.

(10) Patent No.: US 9,809,928 B2
(45) Date of Patent: *Nov. 7, 2017

(54) PRODUCT TO PROMOTE FLUID FLOW

(75) Inventors: David E Fish, Bellevue, WA (US); Hugh West, Seattle, WA (US); Linda A Beltz, Gig Harbor, WA (US)

(73) Assignee: INTERNATIONAL PAPER COMPANY, Memphis, TN (US)

( * ) Notice: Subject to any disclaimer, the term of this patent is extended or adjusted under 35 U.S.C. 154(b) by 1766 days.

This patent is subject to a terminal disclaimer.

(21) Appl. No.: 11/627,291

(22) Filed: Jan. 25, 2007

(65) Prior Publication Data

US 2008/0179027 A1     Jul. 31, 2008

(51) Int. Cl.
    *D21H 11/16*      (2006.01)
    *A61F 13/537*      (2006.01)
    *A61F 13/53*      (2006.01)

(52) U.S. Cl.
CPC ............ *D21H 11/16* (2013.01); *A61F 13/537* (2013.01); *A61F 2013/530007* (2013.01)

(58) Field of Classification Search
CPC ....... D21H 11/16; D21H 11/00; A61F 13/537; A61F 2013/530007; A61F 13/15; A61F 13/15707; A61F 13/532; A61F 13/512
USPC ....... 428/359, 402, 326, 392, 393, 364, 407; 162/9, 146, 218, 100, 90, 13, 157.6; 156/268, 201, 202, 204, 216, 227, 257, 156/270, 308.2, 308.4; 604/366, 378, 604/385.1, 385.2, 386, 368, 381
See application file for complete search history.

(56) References Cited

U.S. PATENT DOCUMENTS

| | | | |
|---|---|---|---|
| 3,003,911 A * | 10/1961 | Lindstrom et al. | ........... 162/100 |
| 3,901,236 A | 8/1975 | Assarsson et al. | |
| 4,986,882 A | 1/1991 | Mackey et al. | |
| 5,549,589 A * | 8/1996 | Horney et al. | ................ 604/366 |
| 5,957,906 A | 9/1999 | Roe et al. | |
| 6,092,302 A | 7/2000 | Berrigan | |
| 6,203,654 B1 * | 3/2001 | McFall et al. | ................ 156/268 |
| 6,280,667 B1 | 8/2001 | Koenig et al. | |
| 6,673,984 B1 | 1/2004 | Roe et al. | |

(Continued)

FOREIGN PATENT DOCUMENTS

| | | |
|---|---|---|
| EP | 843042 A1 * | 5/1998 |
| EP | 1 418 268 A2 | 5/2004 |
| WO | 2005/021458 A1 | 3/2005 |
| WO | 2005/021458 A1 | 10/2005 |

OTHER PUBLICATIONS

Dahiya, A. et al. Wet-Laid Nonwovens. Apr. 2004. http://www.engr.utk.edu/mse/Textiles/Wet%20Laid%20Nonwovens.htm.*

(Continued)

*Primary Examiner* — Alicia Chevalier
(74) *Attorney, Agent, or Firm* — Christensen O'Connor Johnson Kindness PLLC

(57) ABSTRACT

A cellulose pulp particle having the shape of a general prismatoid having two parallel bases, the pulp particle comprising pulp fibers in a wet laid pulp sheet form, one of the bases having an area that is equal to or greater than the area of the other base, the area of the larger base being equal to or less than 30 mm$^2$ and equal to or greater than 8 mm$^2$, the height of the particle, the perpendicular distance between the bases, being equal to or greater than 0.9 mm and equal to or less than 5 mm.

14 Claims, 11 Drawing Sheets

(56) References Cited

U.S. PATENT DOCUMENTS

| | | | |
|---|---|---|---|
| 6,709,550 B2 * | 3/2004 | Holz et al. | 162/130 |
| 7,201,825 B2 * | 4/2007 | Dezutter et al. | 162/9 |
| 7,306,846 B2 * | 12/2007 | Dezutter et al. | 428/402 |
| 2003/0070776 A1 * | 4/2003 | Crow et al. | 162/9 |
| 2003/0213572 A1 | 11/2003 | Vrbanac et al. | |
| 2004/0041040 A1 | 3/2004 | Dezutter et al. | |
| 2004/0079499 A1 | 4/2004 | Dezutter | |
| 2005/0178518 A1 | 8/2005 | West et al. | |
| 2005/0225009 A1 | 10/2005 | Sain et al. | |
| 2006/0006564 A1 | 1/2006 | Maldas et al. | |
| 2007/0190300 A1 | 8/2007 | Bell et al. | |
| 2008/0179027 A1 | 7/2008 | Fish et al. | |
| 2008/0182104 A1 * | 7/2008 | Fish et al. | 428/403 |

OTHER PUBLICATIONS

Smook, Gary A., Manufacturing Techniques for Specific Paper and Board Grades, Handbook for Pulp & Paper Technologists, Third Edition, Angus Wilde Publications, Inc., Bellingham, WA, 2002, p. 311.

Dictionary of Paper, 5th Edition, TAPPI, TAPPI Press, Atlanta, GA 1996, p. 308.

Casey, James P., Pulp and Paper Chemistry and Chemical Technology, Second Edition, vol. III: Paper Testing and Converting, Interscience Publishers, Inc., US, 1952, p. 1270.

Extended European Search Report dated Feb. 13, 2017, filed in corresponding European Application No. 10005782.7, filed Jun. 3, 2010, 7 pages.

* cited by examiner

PRODUCT TO PROMOTE FLUID FLOW

The present invention relates to a product for improving flow of liquids of all viscosities. More specifically, this invention is an inexpensive and easily manufactured material that will provide improved bodily fluid and waste flow in a disposable, absorbent, sanitary article.

Absorbent or sanitary disposable articles such as diapers, adult incontinence products or sanitary napkins usually have an acquisition/distribution member against a storage member. These are housed between a top sheet, which rests against the user and through which fluid passes, and a backsheet which holds the liquid within the product and through which fluid does not pass. The acquisition/distribution member receives fluid and distributes and transfers the fluid to the storage member in which the fluid is held. The transfer should be fast enough so that fluid and other matter do not leak around the edges of the sanitary article or transfer back through the top sheet to the skin of the user.

The advantages and requirements of an acquisition/distribution member in sanitary articles are well known in the art. Such members will rapidly acquire and briefly contain low viscosity bodily fluids such as urine during elimination where a relatively high volume of fluid on the order of 50 ml or more is presented in a rather short time (on the order of 10 sec to 1 minute) thereby preventing fluid leaks out of the article. This member will then provide for rapid fluid transfer to the rest of the article where the fluid is stored allowing itself to be available for repeated fluid insults. To be successful this layer must provide channels that permit rapid flow even under a weight load caused by the wearer of article. It should be of low compressibility to maintain these channels but yet be flexible to provide comfort to the wearer. In addition, it is desirable for this member to maintain a relatively dry top layer to keep the skin of the wearer dry. One material used in such acquisition/distribution members is crosslinked pulp fiber which will maintain its bulk density when wet and under a load. Another is spun blown synthetic fibers.

Good management of higher viscosity fluids such as menses, loose stools, etc., has some additional requirements. Structures and/or materials that meet those requirements often will have features such as large voids to immediately accumulate the high viscosity fluid. The surrounding structure or material should then have the capability to absorb water from the fluid thereby raising the viscosity of the high viscosity fluid even further to prevent leakage out of the article. The absorbed fluid should then preferably migrate from this layer into the highly absorbent materials in the storage layer below. This structure and/or materials must still be moderately incompressible but flexible as described above for low viscosity fluid management.

The provision of these void spaces requires special designs of the acquisition/distribution layer and special equipment to form these designs. This adds to the cost of the absorbent product.

Pulp is normally used in sanitary articles, but it is normally used in fiber form. Pulp for use in the fiber form is usually supplied to the sanitary product plant as rolled sheets or flat cut sheets. Because of the simple production methods, pulp sheets are a highly economical form of pulp. The rolled sheet has a typical basis weight of 750 g/m$^2$ (grams per square meter) and a caliper of 1.2 mm (millimeters). The cut sheet has the same basis weight and is about 0.75 m (meter) by 0.76 m and a caliper of 1.2 mm. As explained later, the caliper and basis weight may vary. The product is then shipped to manufacturers of sanitary disposable products who then disintegrate the sheets into individual fibers. These fibers may be used in the acquisition/distribution member or the storage member. The fibers give the sanitary products bulk, softness, and high absorbency. A typical pulp for sanitary articles is Southern softwood pulp typically produced from Loblolly Pine and Slash Pine, trees common in the Southeastern United States.

The sanitary article must be comfortable to the wearer, must acquire quickly, hold fluid and high viscosity material and must be unobtrusive. The acquisition/distribution member is important to obtaining these results by quickly acquiring and distributing the fluids from fluid material and high viscosity material. There is a need for a simple solution for an acquisition/distribution layer that may be used to acquire quickly and hold high viscosity fluids and normal fluids, be easily produced, and be comfortable and unobtrusive when used in a disposable garment such as diapers, feminine hygiene products and adult incontinence products. The inventors have devised a simple solution that provides good acquisition and good distribution.

Applicant realizes that some of the terms used in this application have different definitions depending on the source. For example, the definitions found in *Solid Mensuration*, 2$^{nd}$ Edition, by Willis F. Kern and James R. Bland, published by John Wiley and Sons, Inc., 1938, may not agree with the definitions found in *The American Heritage Dictionary of the English Language*, 1979 edition, published by Houghton Mifflin, and neither may agree with the definitions found in *Webster's New Collegiate Dictionary*, 1973 edition published by G. and C. Merriam Company. For this reason, applicant will use the following definitions for the terms being used in this application.

As used herein, the term "general prismatoid" is defined as a solid having at least one pair of sides that are "elements" of parallel planes. These elements are referred to as the "bases" of the general prismatoid. For the purposes of this application these elements are surfaces. For the purposes of this application, a general prismatoid does not include spheres. For shapes that have more than one pair of parallel sides, the bases will be defined as the pair of opposed parallel sides that are separated by the smallest distance.

As used herein, a "simple prismatoid" is a polyhedron having all vertices lying in one of two parallel planes. A polyhedron is a solid bounded by polygons. A polygon is a closed plane figure bounded by three or more line segments. A simple prismatoid would include, for example, cubes, rectangular parallelepipeds, prisms, and pyramidal frustums. For the purposes of this application, a simple prismatoid is a type or subset of a general prismatoid as defined herein.

As used herein, "cuboid" is synonymous with "rectangular parallelepiped" and is a polyhedron whose six faces are all rectangles. A cuboid is a type of simple prismatoid.

As used herein, the term "square cuboid" is defined as a cuboid with at least one pair of opposite sides being squares. A square cuboid is a type of cuboid.

As used herein, "cylindrical surface" is a surface generated by a moving straight line ("generator") which is always parallel to a fixed line, and which always intersects a fixed plane curve ("directrix") not in the plane with the fixed line. If the directrix of the cylindrical surface is a closed curve, the surface is "closed". The directrix may be a circle, ellipse, flower shaped, or any irregular curve As used herein, "cylinder" is a solid bounded by a closed cylindrical surface and two parallel planes. A cylinder would be a type of general prismatoid as defined herein.

Figure 3:
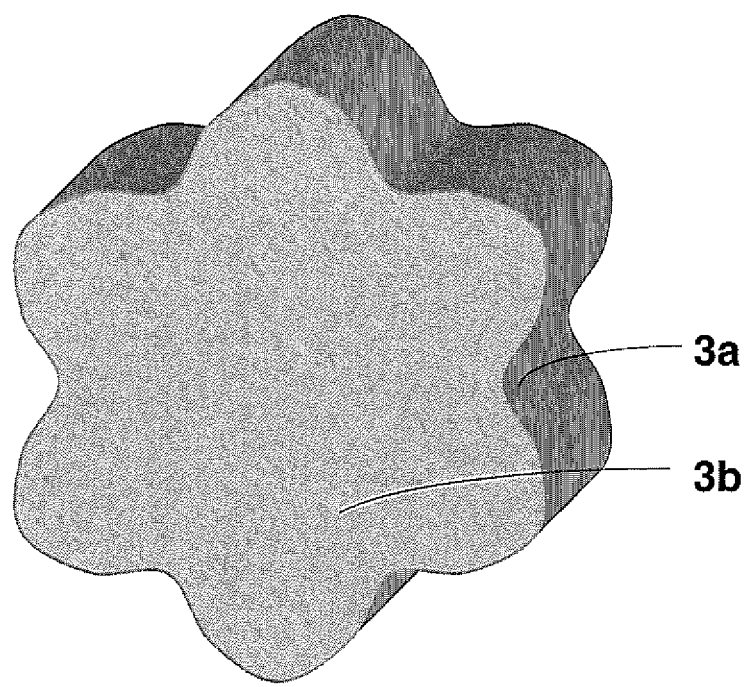

As used herein, "right cylinder" is a cylinder where the cross sections all lie directly on top of one another. FIG. 3 illustrates an example of a right cylinder.

Figure 2:
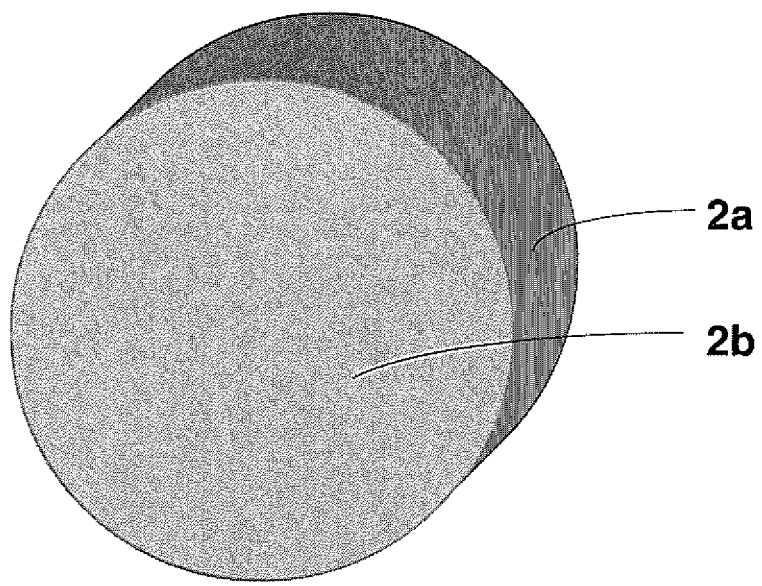

As used herein, "right circular cylinder" is defined as a right cylinder where the bases are circular in shape. FIG. 2 illustrates an example of a right circular cylinder. A right circular cylinder is a subset of right cylinders.

As used herein, the term "height" refers to the perpendicular distance between the bases of a "general prismatoid" as defined herein.

The present invention relates to a product for improving flow of liquids of all viscosities, especially urine, menses, and loose stools or feces. It is useful in absorbent or sanitary products such as diapers, feminine care products and adult incontinence products. It can be easily produced and exhibits improved acquisition properties.

In one embodiment the invention comprises particles which are general prismatoids. In one embodiment the particles have small squares, circles, any other simple geometric shape, or even more complex shapes as at least one of the parallel bases of the general prismatoid. In another embodiment both of the bases of the particles have the same shape. These general prismatoids have been cut, punched, or otherwise shaped from a sheet of absorbent pulp. These parallel bases would be the surfaces of the pulp sheet from which the particles are formed.

In manufacturing an absorbent article, it is usual for the back sheet to be laid down, the storage core or member to be placed on top of the back sheet, the acquisition/distribution member to be placed on top of the storage member and the top sheet to be placed on the acquisition/distribution member. There are usually many other elements of the absorbent article which are placed on the article during its manufacture but the back sheet, storage member, acquisition/distribution member and top sheet will only be considered here.

The back sheet is usually polyethylene or some other liquid impervious material. The storage member is usually pulp fibers into which superabsorbent particles are placed. The pulp fibers and superabsorbent particles are air laid onto the back sheet to form the storage member. The acquisition/distribution member would be placed on the layer of pulp fibers that comprises the storage core. The placement of the acquisition/distribution member will depend on the diaper design. The acquisition/distribution member may be only in the area of the insult and transfer the insult to the storage layer and depend on the wicking capability of the storage layer to move the fluid throughout the storage layer. On the other hand the acquisition/distribution member may be over a larger area of the storage layer so that the wicking ability of the acquisition/distribution layer can be used to also spread the fluid throughout the storage layer.

A top sheet is then placed over the acquisition/distribution member, and the storage member and the top sheet and back sheet are adhered together. During this process pressure is placed on the article to adhere the top sheet and back sheet together and densify the article so that it will have a narrow contour.

In forming the acquisition/distribution member, the particles would be dropped and scattered onto the storage layer over the required area to form the acquisition/distribution member.

In one embodiment the dimension of the shapes of the bases of the particles would be larger than the thickness of the pulp sheet from which they were produced. When scattered onto an absorbent article, particles with these dimensions will tend to orient themselves with the cut edges normal to the article and original pulp sheet surfaces parallel to the article. Misalignment of the pieces will be tend to be corrected during the finishing of the absorbent article where forces normal to the article are applied thereby realigning the cut pieces.

In another embodiment, the particles can be surface treated with chemicals to modify the absorptive properties or flow properties, in a positive or negative way. The pulp sheet can be surface treated before manufacture of the particles. The faces of the particles can be treated with hydrophobic or hydrophilic chemicals. A hydrophilic surface treatment will increase the absorption and retention of fluid in the particle. A hydrophobic treatment will increase fluid flow through the acquisition/distribution member. A softening chemical will provide comfort to the user of an article incorporating the particles. In one embodiment, one base of the particle could be treated with a hydrophilic chemical and the other base treated with a hydrophobic chemical to obtain the attributes of both of these treatments. These treatments would be placed on the pulp sheet prior to forming particles from the pulp sheet. The chemicals could be placed on the pulp sheet by a transfer roll such as a size press. Hydrophilic chemicals that can be used are glycerol, corn syrup, sugar, calcium chloride, magnesium chloride, poly glycols, sorbitol, and many others. Hydrophobic chemicals that can be used are styrene acrylic esters, styrene acrylic acids, fluoro-compounds, alkyketene dimer, and many others. Other chemicals that could be added to make the surfaces hydrophobic are starch and polyvinyl alcohol among others. Addition rates could be as low as 0.01 pounds per ton and as high as 100 pounds per ton.

When chemicals are placed on the surfaces of the pulp sheet, which will become the bases of the particle, the chemical will penetrate into the sheet for some distance, depending on the fiber being used, the density of the sheet, the amount of chemical and the pressure with which the chemical is applied. The chemicals can be sprayed or coated onto the sheet before or after drying.

The pulp sheet may be treated during manufacture. The chemicals can be added to the process during sheet manufacture and before drying. The location of addition will depend on the chemical. A chemical that can be washed out with the water will be placed in the sheet late in the process. A chemical that will not be washed out with the water can be placed in the sheet earlier in the process. In some instances a hydrophilic chemical may be added to the pulp sheet during manufacture and a hydrophobic chemical placed on the surface of the pulp sheet prior to the formation of the particles.

In a further embodiment the particles can be treated with other chemicals to enhance other performance or aesthetic or comfort attributes. The pulp sheet can be treated before manufacture of the particles or the particles can be treated after manufacture. Chemicals that add hydrophobicity will allow for faster acquisition rates. Chemicals that add hydrophilicity will allow for great absorbency, fluid capacity, and dewatering capability. Dyes may be added to modify appearance. Softening chemicals may be added for comfort. Typical softening agents are sorbitol and glycerin.

In additional embodiments the particles may include polymer films, adhesives, more than one layer of pulp or other materials such as different fibers or chemically modified fibers. The pulp sheet can be combined with other materials such as polymer films, adhesives, additional pulp sheets, or other materials before manufacture of the particles. Different fibers or chemically modified fibers could be used in the production of the pulp sheet. Any of these can modify performance parameters of the final particles. High bulk fibers, both cellulosic and polymeric, could be added to raise the bulk of the particle to provide some softness. Hydrophobic fibers, both cellulosic and polymeric, could be added to modify the acquisition rate and fluid retention capacity of the final particles. Films such as polyethylene, nylon or PET can be bonded to the pulp sheet prior to forming into particles.

The pulp particles are manufactured from a pulp sheet. The pulp sheet is wet laid and there will be a random orientation of the fibers. The fibers will tend to align primarily along the machine direction of the sheet and to a slightly lesser extent along the cross direction of the sheet. There is some alignment along the direction normal to the faces of the sheet, commonly named the z-direction. In a wet laid pulp sheet the fibers attach to each other by hydrogen bonding.

Southern pine fibers are used as absorbent fibers because they tend to have a large bore and higher stiffness than other fibers, which lead to its high fluid absorbency. This fiber morphology combined with the typical fiber orientation means there will be greater expansion of the particle when a southern pine fiber is used.

Several embodiments of the present invention are illustrated in the drawings.

Figure 1:
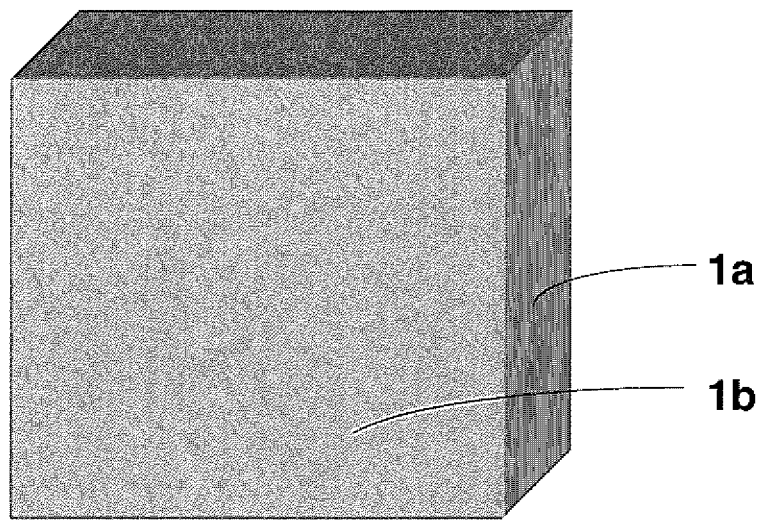
FIGS. 1-9 are isometric views of different embodiments of the invention.

FIG. 1 is an isometric view of an embodiment of the present invention showing a "general prismatoid" having square shaped bases in which 1a is the cut edge of the particle and bases 1b are the surfaces of the original pulp sheet from which this particle was formed. The square shaped base is exemplary. The base may be rectangular, have undulating edges or jig-saw shaped edges. It may have any number of cut sides. It may have 3 up to ten or more sides. It may be a general prismatoid, a simple prismatoid, a cuboid or a square cuboid. The planes of the bases are substantially parallel because they are the surfaces of the original pulp sheet.

FIG. 2 is an isometric view of a second embodiment of the present invention showing a cylindrical particle in which 2a is the cut edge of the particle and bases 2b are the surfaces of the original pulp sheet from which this particle was formed. The edges of the bases are shown as circular. Again this is exemplary. The edges can be any continuous shape. Among other shapes it may be a general cylinder, a right general cylinder or a right circular cylinder. These specified shapes are not limiting but only given as examples. The planes of the bases are substantially parallel because they are the surfaces of the original pulp sheet.

FIG. 3 is an isometric view of a third embodiment of the present invention showing cylindrical particle in which 3a is the cut edge of the particle and base 3b is the surface of the original pulp sheet from which this particle was formed. This exemplifies a cylindrical particle in which the edges of the bases are other than a circle. The edges are shown as flower shaped. This shape is not limiting but only given as an example. The planes of the bases are substantially parallel because they are the surfaces of the original pulp sheet.

Figure 4:
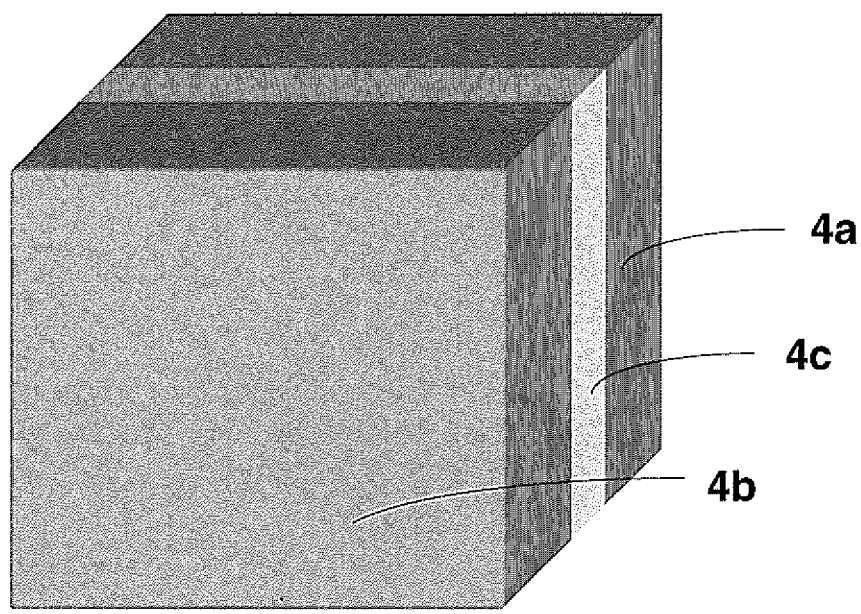

FIG. 4 is an isometric view of a fourth embodiment of the present invention showing a general prismatoid particle cut from a material in which two pulp sheets 4a and 4b are adhered together with an adhesive 4c. The outer surfaces of the sheets 4a and 4b form the bases of the general prismatoid. It may be a general prismatoid, a simple prismatoid, a cuboid or a square cuboid. These shapes are not limiting but only given as examples. In the drawing the edges of the bases form a square. The square shaped base is exemplary. The base may be rectangular, have undulating edges or jig-saw shaped edges. It may have any number of cut sides. It may have 3 up to ten or more sides. The planes of the bases are substantially parallel because they are the surfaces of the original adhered pulp sheets. The two pulp sheets are exemplary. Two or more pulp sheets may be adhered together.

Figure 5:
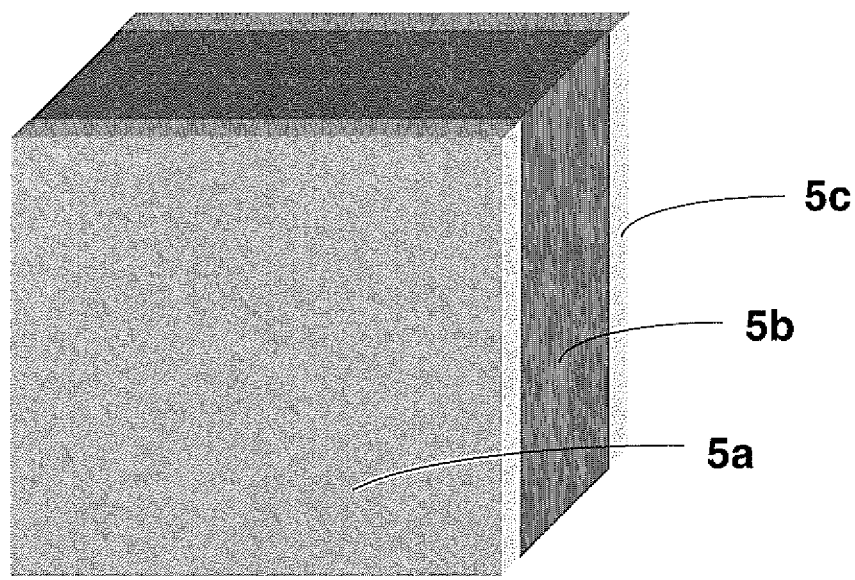

FIG. 5 is an isometric view of a fifth embodiment of the present invention showing a general prismatoid particle 5b cut from a pulp sheet and having on one base a lamination film 5a and on the other base a lamination film 5c. The lamination films are exemplary of treating the bases of the particle with either a film or a chemical such as a hydrophilic or hydrophobic chemical. The laminations or treatment chemicals would be placed on the pulp sheet prior to the manufacture of the particles. The films could be either heat laminated or adhered to the pulp sheet. It may be a general prismatoid, a simple prismatoid, a cuboid or a square cuboid. In the drawing the edges of the bases form a square. These shapes are not limiting but only given as examples. The square shaped base is exemplary. The base may be rectangular, have undulating edges or jig-saw shaped edges. It may have any number of cut sides. It may have 3 up to ten or more sides. The planes of the bases are substantially parallel because they are the surfaces of the original pulp sheet.

Figure 6:
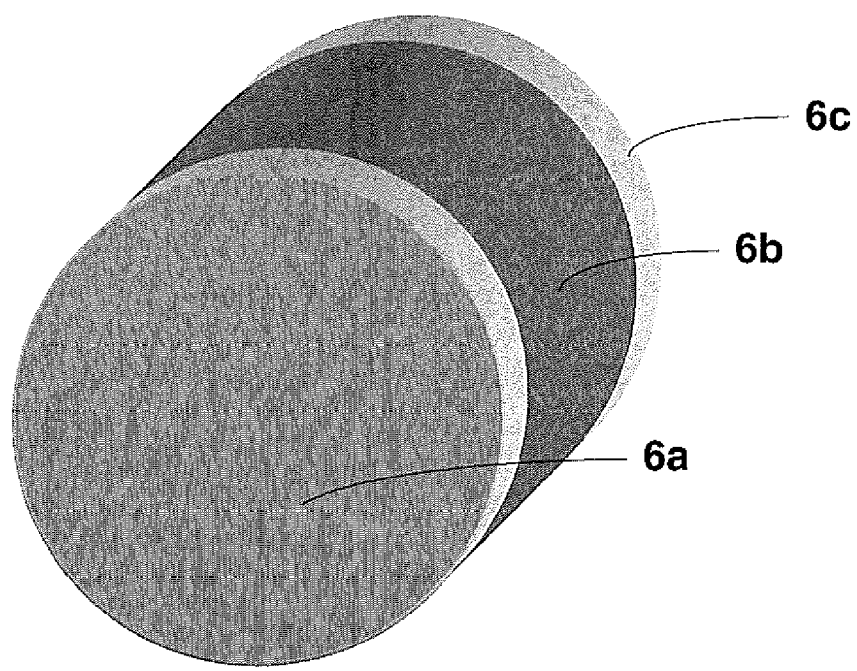

FIG. 6 is an isometric view of a sixth embodiment of the present invention showing a cylindrical particle 6b cut from a pulp sheet and having on one base a lamination film 6a and on the other base a lamination film 6c. The lamination films are exemplary of treating the bases of the particle with either a film or a chemical such as a hydrophilic or hydrophobic chemical. The laminations or treatment chemicals would be placed on the pulp sheet prior to the manufacture of the particles. The films could be either heat laminated or adhered to the pulp sheet. Among other shapes it may be a cylinder, a right general cylinder or a right circular cylinder. These specified shapes are not limiting but only given as examples The edges of the bases are shown as circular. Again this is exemplary. The edges can be any continuous shape. The planes of the bases are substantially parallel because they are the surfaces of the original pulp sheet.

Figure 7:
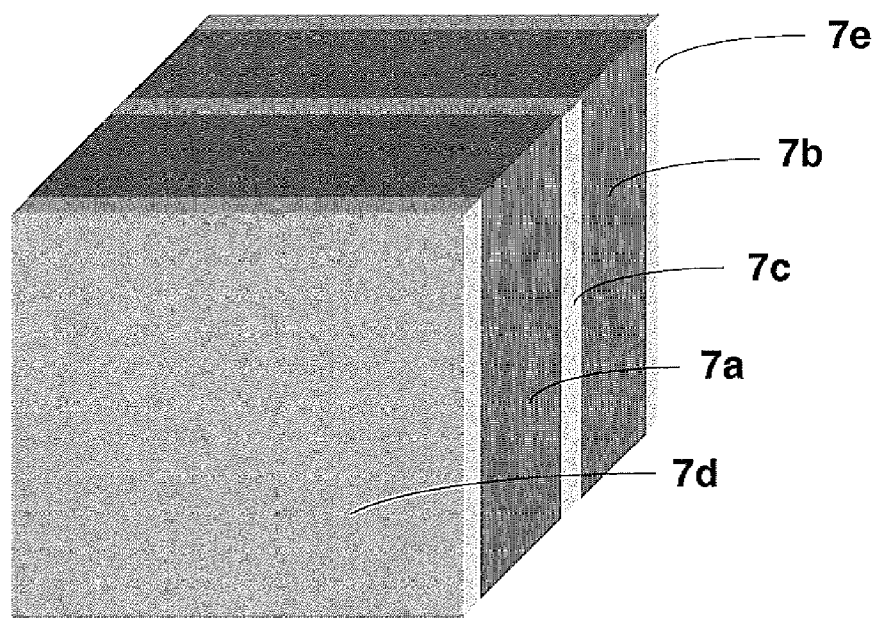

FIG. 7 is an isometric view of a seventh embodiment of the present invention showing a general prismatoid particle cut from two pulp sheets 7a and 7b adhered together with an adhesive 7c and having a lamination film 7d on one base and a lamination film 7e on the other base. The lamination films are exemplary of treating the bases of the particle with either a film or a chemical such as a hydrophilic or hydrophobic chemical. The laminations or treatment chemicals would be placed on the pulp sheets prior to the manufacture of the particles. The films could be either heat laminated or adhered to the pulp sheet. It may be a general prismatoid, a simple prismatoid, a cuboid or a square cuboid. These shapes are not limiting but only given as examples. In the drawing the edges of the bases form a square. The square shaped base is exemplary. The base may be rectangular, have undulating edges or jig-saw shaped edges or have a single unitary edge of any shape such as a circle or ellipse or flower shaped. It may have any number of cut sides. It may have 3 up to ten or more sides. The planes of the bases are substantially parallel because they are the surfaces of the original pulp sheets.

Figure 8:
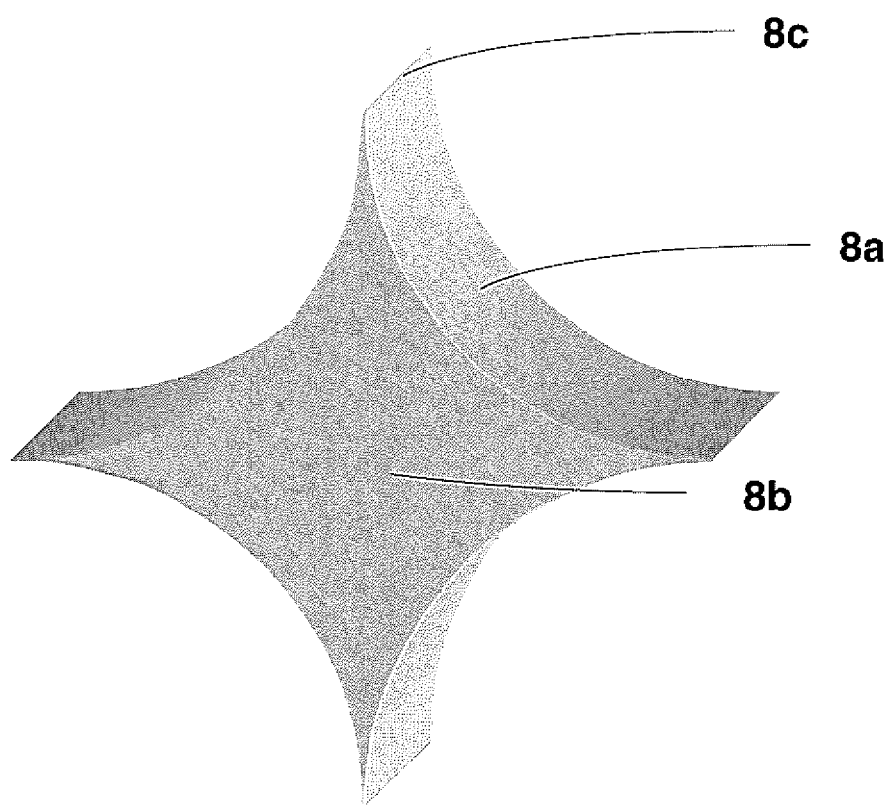

FIG. 8 is an isometric view of an eighth embodiment of the present invention showing a general prismatoid particle formed from the portion of the pulp sheet left over after the general cylindrical particles have been cut from a pulp sheet. It is the section between 4 tangential cylindrical portions and is formed of four concave surfaces 8a that meet at points 8c. A base 8b is also shown. The shape of the concave surfaces will depend on the particular shape of the cylinders.

Figure 9:
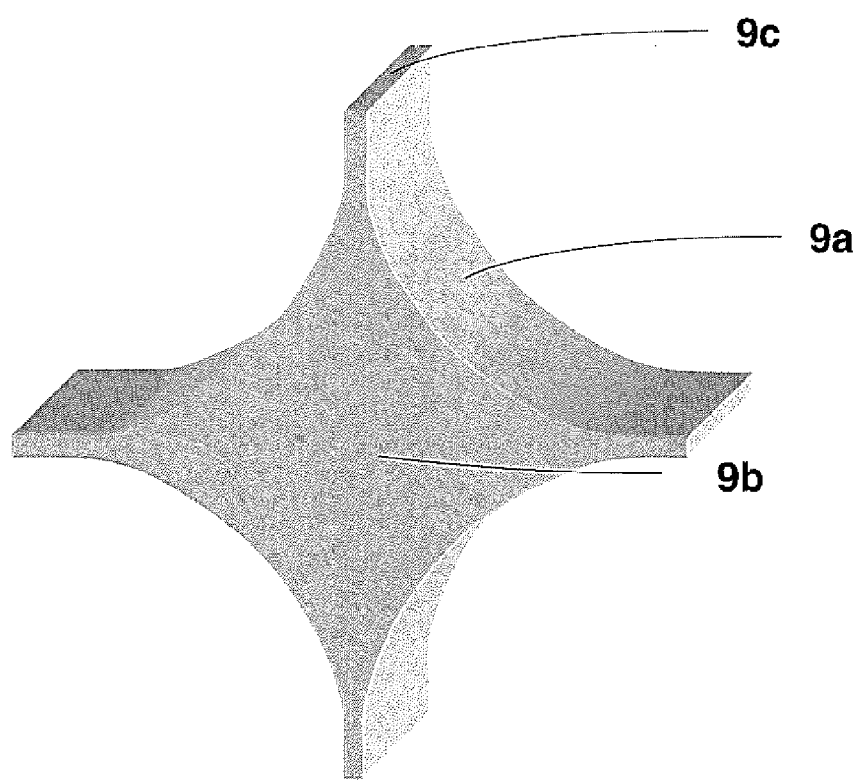

FIG. 9 is an isometric view of an ninth embodiment of the present invention showing a general prismatoid particle formed from the portion of the pulp sheet left over after the general cylindrical particles have been cut from a pulp sheet. It is the section between 4 cylindrical portions that are spaced from each other. and is formed of four concave surfaces 9a that are joined at their ends by planes 9c. A base 9b is also shown. The shape of the concave surfaces will depend on the particular shape of the cylinders.

These embodiments are exemplary of the shapes and types of particles that can be formed. It should be understood that any of the particle shapes may be made of more than one ply and may be treated as described herein.

The bases of the particle may have the same or different areas. The area of the largest base, if the bases have different areas, or of a base, if the bases have the same area, will be equal to or less than 35 mm$^2$ and equal to or greater than 8 mm$^2$. Although square particles are shown, the length can be greater than the width. The thickness or height of the particle will be from 0.9 to 1.5 mm if the particle is a single thickness particle, from 1.8 mm to 3 mm if the particle is a double thickness particle, and from 2.7 mm to 4.5 mm if the particle is a triple thickness particle. The height can be as high as 6 mm. As described above the dimension of the base of the particle should be greater than the thickness of the particles so that the particles will lie on their bases in the absorbent article. As described below the thickness of a pulp sheet has a maximum dimension so there may be two or more thicknesses of pulp in some embodiments.

The dimensions of the particle must be small if they are being used in an absorbent article such as a diaper, a feminine care product or an adult incontinent product. They must lie down within the garment and be form fitting to the contours of the body. They must provide comfort to the wearer. A large particle will not provide these attributes. Also they must be able to distribute evenly. Smaller particles will tend to distribute more evenly than large particles. It has been found that the smaller particles will absorb more quickly in repeated insults as compared to larger particles. This can be seen in the examples. It has also been found that round particles absorb more quickly in repeated insults than square or rectangular particles. This can also be seen in the examples. The particles cannot be too small or they will not lay right in the absorbent article.

These particles are formed from pulp sheets or enhanced pulp sheets. In practice a pulp sheet made from any pulp may be used.

The raw material for pulp may be any hardwood or softwood or other material commonly used for pulp, such as bagasse. It may be made from a chemical, mechanical, thermomechanical or chemithermomechanical process. In one embodiment a kraft pulp made from southern U.S. softwoods may be used. In another embodiment a kraft pulp made from southern U.S. pine, such as loblolly pine, may be used.

A chemical pulp is manufactured by cooking the raw material in an alkali such as sodium hydroxide. The hydroxide may be combined with a sulfate to manufacture kraft pulp. The hydroxide may be combined with a sulfite to manufacture sulfite pulp. In the cook the lignin and hemicellulose are solubilized and separated from the cellulose. The yield of the pulp will depend on the amount of lignin and hemicellulose removed. Usually more hemicellulose and lignin is removed in sulfite pulping than in sulfate pulping. The hemicellulose and lignin are washed from the pulp and the pulp is then brightened with oxidizing agents by bleaching. Chlorine dioxide and chlorine are typically used as bleaching agents.

A mechanical pulp is manufactured by grinding the raw material into fibers. The lignin and hemicelluloses in the raw material will for the most part remain with the fiber.

A thermomechanical pulp is manufactured by steaming the raw material and then grinding the raw material into fibers. The steam softens the raw material and makes it easier to grind into fibers. The steam may remove some of the hemicellulose and lignin from the fiber during the process.

A chemithermomechanical pulp is manufactured by treating the raw material with chemicals and steam and then grinding the raw material into fibers. The chemicals and steam may remove some of the hemicellulose and lignin from the fibers.

The process, after forming the fibers, is the same for any of the fibers. The fibers are slurried in water and the slurry of fibers and water is flowed onto a moving screen. The purpose of the rest of the process is to remove water from the fibers and to cause the fibers to form into a self-supporting web, either by hydrogen bonding between the fibers in the case of chemical pulp, or by intertwining and hydrogen bonding in the case of mechanical, thermomechanical and chemithermomechanical fibers.

Water is removed from the fibers as they pass along the screen. The fibers are then calendered between rolls to further remove water and to press the fibers together. The fibrous web is then passed to a drier to further remove water. The drier can be a through air drier or a steam heated can drier. In any case, the pulp mat must be thin enough to be thoroughly dried. Because of the requirements of the process, the pulp mat will have a thickness of from 0.9 mm to 1.5 mm. A typical pulp mat can have a thickness of 1.2 mm.

In the wet end of the pulp process, hydrophilic chemicals can be added to the pulp. These chemicals will remain in the pulp sheet.

The thickness of the pulp mat will dictate the number of thicknesses in the particle.

The basis weight of the pulp sheet can also vary because of the pulp being used and the manufacturing techniques. It may vary from 600 g/m$^2$ to 1000 g/m$^2$.

The pulp sheet can be used as is for the manufacture of the particles or it can be adhered to another pulp sheet to form a double thickness pulp sheet. It can also be adhered to other pulp sheets to form multiple thickness pulp sheets before the manufacture of the particles. The outer surface of the pulp sheet or sheets may be treated in a size press or other apparatus to apply material to the sheet. It may also have film laminated to its outer surface.

In commercial practice the particles would be formed by cutting the particles out of the pulp sheets or laminated pulp sheets using a rotary die cutter having the required particle shape and size, or by other cutting devices known in the art.

The pulp sheet used for the particles in the examples below is commercially available Weyerhaeuser Columbus Pine pulp manufactured in Columbus, Miss. It contained only pulp fibers and contained no modified fibers or other types of fibers.

The adhesive used for adhesive laminations in the examples was a 2" wide commercial splicing tape, product number AR7418 CO#E5863, produced by Adhesive Research Inc., Glen Rock, Pa. This tape has an adhesive on both sides. The adhesive on one side is attached to a removable backing. In practice any adhesive that will adhere two sheets of pulp together may be used. It may be in sheet form or may be a liquid that can be coated on the pulp sheet by brush, roll or curtain coating. In any embodiment the adhesive must coat the entire surface of a roll so that the pulp portions forming the particles taken from the adhered rolls will be adhered together.

The adhesive laminated pulp sheet used in the examples was produced by applying strips of the Adhesive Research adhesive tape described above to one side of a pulp sheet. The strips were laid side-by-side until the whole surface of the pulp sheet had the adhesive strips adhered to it. The tape backing was removed thereby exposing the other adhesive layer. A second pulp sheet was then pressed onto the first sheet resulting in the adhesive lamination of the two sheets. In practice the adhesive would be applied to one surface of a pulp sheet. The adhesive could be two sided adhesive material, or a liquid adhesive that is spread or sprayed or curtain coated onto the surface of the pulp sheet. The adhesive may be spread by a roll coater or other type of coater. Another sheet of pulp would be placed on the first sheet of pulp and the two sheets adhered together. The process would be repeated if a three ply pulp sheet were to be used.

The lamination film used to produce the laminated pulp sheet was a 3.0 mil Doculam CR film available from Binder Products, Seattle, Wash. They are composed of general purpose polyesters. The laminator used was a model BA-PS27 made by Banner American Products, Inc., Rancho California, Calif.

Pulp sheets having film laminated to their bases were produced by feeding the pulp sheet into the Banner American laminator at a speed setting of 10, roll temperatures of 325° F., top and bottom, and maximum pressure with the Doculam lamination film on the top and bottom unwinds. The pulp sheet had film laminated to its top and bottom surfaces. Pulp sheets adhered together to form a two ply sheet had film laminated to their bases in the same manner.

In practice any type of laminating film may be used to provide a film on the exterior outer bases of the particles. The laminating films may be adhered by heat or by an adhesive.

Twelve types of particles were provided for the examples.

Particle 1 was a square cuboid as shown in FIG. 1. It was 3 mm long, 3 mm wide and the perpendicular distance between the bases was 1.2 mm. The areas of the bases of a particle were equal and the area of each base was 9 mm$^2$. The particles were cut from a single thickness pulp sheet with a conventional paper cutter. The particles had no surface coating or lamination.

Particle 2 was also a square cuboid as shown in FIG. 1. It was 5 mm long, 5 mm wide and the perpendicular distance between the bases was 1.2 mm. The areas of the bases of a particle were equal and the area of a base was 25 mm$^2$. The particles were punched from a single thickness pulp sheet using a hand paper punch produced by Fiskars, item 23587097. The particles had no surface coating or lamination.

Particle 3 was a square cuboid as shown in FIG. 4. It was 5 mm long, 5 mm wide and the perpendicular distance between the bases was 2.4 mm. The areas of the bases of a particle were equal and the area of a base was 25 mm$^2$. The particles were cut from a double thickness pulp sheet. The double thickness pulp sheet was formed by adhering two pulp sheets together as described in the above description of forming a double thickness pulp sheet. The particles were cut using a conventional paper cutter. The particles had no surface coating or lamination.

Particle 4 was a square cuboid as shown in FIG. 5. It was 5 mm long, 5 mm wide and the perpendicular distance between the bases was 1.2 mm. The areas of the bases of a particle were equal and the area of a base was 25 mm$^2$. The particles were cut from a single thickness pulp sheet using a conventional paper cutter. The particle had a PET surface lamination on both bases.

Particle 5 was a square cuboid as shown in FIG. 7. It was 5 mm long, 5 mm wide and the perpendicular distance between the bases was 2.4 mm. The areas of the bases of a particle were equal, and the area of a base was 25 mm$^2$. The particles were cut from a double thickness pulp sheet. The double thickness pulp sheet was formed by adhering two pulp sheets together as described in the above description of forming a double thickness pulp sheet. The particles were cut using a conventional paper cutter. The particle had a PET surface lamination on both bases.

Particle 6 was a right circular cylinder as shown in FIG. 2. It had a diameter of 3 mm and the perpendicular distance between the bases was 1.2 mm. The areas of the bases of the particle were equal and the area of a base was 7 mm$^2$. The particles were punched from a single thickness pulp sheet using a Fiskars punch, item 23517097. The particles had no surface coating or lamination.

Particle 7 was a right circular cylinder as shown in FIG. 2. It had a diameter of 6 mm and the perpendicular distance between the bases was 1.2 mm. The areas of the bases of the particle were equal and the area of a base was 28 mm$^2$. The particles were punched from a single thickness pulp sheet using a Fiskars punch, item 23527097. The particles had no surface coating or lamination.

Particle 8 was a right flower shaped cylinder as shown in FIG. 3. The perpendicular distance between the bases was 1.2 mm. The bases had the same area and each base had a cross sectional area of 26 mm$^2$. The particles were punched from a single thickness pulp sheet using a Fiskars punch, item 23627097. The particles had no surface coating or lamination.

Particles 1A, 2A, 6A, and 7A, are PET surface lamination versions of particles 1, 2, 6, and 7 respectively.

FIG. 9 is an isometric view of the apparatus used for in-house loaded acquisition testing in Example 1. A cylinder 9a is attached to a square plate 9b. The lower half of the apparatus 9c is a matching plate to 9b.

Figure 10:
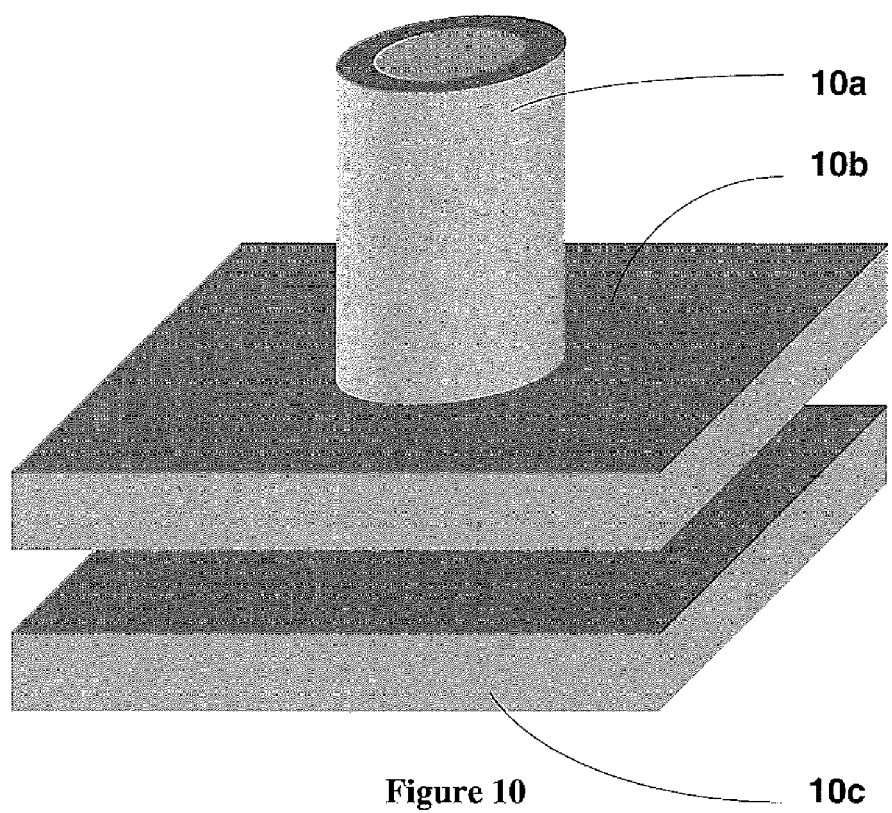
FIG. 10 is an isometric view of the apparatus used for in-house loaded acquisition testing in Example 1.
Figure 11:
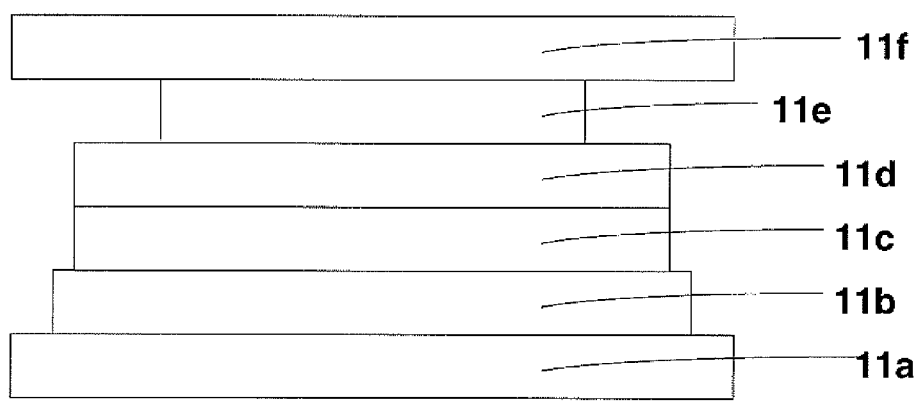
FIG. 11 is a side view schematic of the layers of the commercially available diaper used in Examples 2 and 3.

FIG. 10 is a side view schematic of the layers of the commercially available diaper used in Examples 2 and 3. The outside of the diaper is the backsheet 10a. A tissue 10b lies on top of the backsheet 10a and underneath the fluff and SAP storage core or member 10c. On top of the storage core 10c is another tissue layer 10d. On top of the tissue layer 10d is an acquisition patch 10e, and on top of the acquisition patch 10e is a top sheet 10f which is in contact with the wearer's skin.

The fluff pulp used in the specially made pads was commercially available Weyerhaeuser NB416, manufactured in New Bern, N.C. It was fiberized on a Fitz Hammer Mill, model DAS06, milled with a fixed hammer rotor, at 10,000 rpm, with a breaker bar gap of 3 mils, with a feed rate of about 50 g/minute, with no screen.

The topsheet used in the specially made pads in the examples was a spunbond polyester web, with a basis weight of 15 gram per square meter and a caliper of 1.8 mm, commercially available from First Quality Nonwovens Inc, product #SB1501810.

The tissue used in the specially made pads in the examples was produced by Cellu Tissue Holdings, Alpharetta, Ga., grade 32201-1, with a basis weight of 18 g/m².

EXAMPLE 1

The experimental pads for Example 1 below were produced as follows. Six inch diameter pads containing these pulp sheet particles were made as follows. A mass of 4.0 grams of fiberized NB416 and 1.0 gram of Hysorb 8600 superabsorbent were fed into a six inch airlaid pad former and airlaid onto an 8 inch square of tissue. This resulted in a 5.0 gram airlaid pad with a basis weight of 274 grams per square meter, not including the tissue. Production of such airlaid pads is well known in the art. The airlaid pad was then laid onto an 8 inch square of blotter paper for conveyance. An additional 5.0 grams of additional NB416 fluff was evenly placed on top of the pad for the control pad, and 5.0 grams of pulp particles were evenly placed on top of the other pads. A 6 inch circle of tissue was placed directly on top of the pads. The pad was then placed into a square plastic mold with a 6 inch circular cylinder cut of the center. An 8 inch square of top sheet was then laid on top of the mold. A matching 6 inch circular plug was then placed into the center of the mold on top of the pad resulting in the corners of the top sheet extending out beyond the plug. Two small 0.5 mm thick metal shims were placed on top of the square mold on opposite corners. The mold and its contents were then put between two 12 inch square aluminum plates and compressed at force of 7 tons on a Wabash hydraulic press, model 125-15-SIMX, manufactured by Wabash MPI, Wabash, Ind. The mold surrounding the pad was removed, and the corners of the topsheet were smoothed back down. The caliper of the pad was measured. If the pad was not in the target caliper range of 2.40-2.60 mm, the compression procedure was repeated until the target caliper was achieved.

The acquisition test frame was manufactured in-house and is shown in FIG. 9. It can be described as follows. A Plexiglas tube of a 6 inch height, an outer diameter of 1.5 inches, and an inner diameter of 1.125 inches is permanently attached to the center of a 10 inch square Plexiglas plate. The plate is 5 mm thick with a 1.125 inch hole cut out of the center. This top plate and tube together weigh 425.55 g. The bottom plate is also a 10 inch square, 5 mm thick, but with no holes.

The compressed pads were then placed and carefully centered on the bottom plate of the acquisition test frame, and the blotter paper was carefully removed. The top plate was then carefully centered and placed on top of the pad and the bottom plate. One 125 gram weight was then placed onto each of the four corners of the top plate, with the center of the weight located 1 inch from the two sides forming the corner. A small funnel with a delivery spout of 5 mm in diameter was placed inside the tube on the top plate with the bottom of the funnel being 2⅞ inches above the top surface of the pad. Thirty milliliters of synthetic urine was quickly poured in the funnel and a stopwatch started. The stopwatch is stopped when the meniscus of the synthetic urine falls below the bottom of the tube in the top plate. This time is the acquisition time for the "first insult" and was recorded in seconds. A second stopwatch was started when the first one was stopped. When 20 minutes had elapsed on the second stopwatch, the insult procedure was repeated with a second 30 milliliter dose in exactly the same manner with the recorded time being the second insult time. After another waiting period of 20 minutes, a third 30 milliliter dosage was added in exactly the same manner with the recorded time being the third insult time. The acquisition rate was calculated by taking the insult volume, 30 ml, and dividing by the individual acquisition times. The results for a fluff control and particles 1 through 8 are shown in Table 1.

TABLE 1

| Sample | Number of Tests | Loaded Acquisition Rate (ml/sec) | | | | | |
|---|---|---|---|---|---|---|---|
| | | 1st Insult | | 2nd Insult | | 3rd Insult | |
| | | ave | s.d. | ave. | s.d. | ave. | s.d. |
| NB416 Fluff | 6 | 1.3 | 0.1 | 1.6 | 0.1 | 1.7 | 0.1 |
| Particle 1 | 3 | 2.1 | 0.2 | 4.0 | 0.3 | 3.8 | 0.3 |
| Particle 2 | 1 | 1.4 | — | 2.4 | — | 2.3 | — |
| Particle 3 | 3 | 2.4 | 0.0 | 6.1 | 0.7 | 6.6 | 0.3 |
| Particle 4 | 3 | 1.8 | 0.2 | 3.6 | 0.4 | 3.6 | 0.3 |
| Particle 5 | 3 | 2.6 | 0.4 | 5.9 | 0.7 | 6.5 | 0.4 |
| Particle 6 | 3 | 2.2 | 0.1 | 4.2 | 0.7 | 4.1 | 0.4 |
| Particle 7 | 3 | 1.8 | 0.1 | 2.7 | 0.1 | 2.5 | 0.3 |
| Particle 8 | 1 | 1.9 | — | 3.5 | — | 3.3 | — |

For absorbent products, a fast acquisition is preferable since this indicates that the fluid expressed is rapidly taken up into the product and there is less chance of leakage and would give a more comfortable feeling to the user since the article would feel dryer on the skin. In every case, the particles performed better than an equivalent weight of fluff. The adhesive laminated particles, particles #3 and #4, showed the best acquisition times. It is believed that during the insult, the particles swelled causing a larger void for the insulting liquid to pass more freely. In terms of cross sectional area, the smaller particles performed better. Three mm circles were better than 5 mm circles, and 3 mm squares were better that 4 mm squares. In general, circles seemed better than squares.

EXAMPLE 2

The diapers used for Example 2 and Example 3 were obtained commercially. A cross section of the diaper is shown in FIG. 9. The layers of the diaper, starting from the skin contact side are: nonwoven topsheet, high loft nonwoven acquisition layer, tissue, fluff and SAP (superabsorbent) storage core, tissue, and a polymer film-nonwoven laminate. The diaper had a foam type waistband with Velcro fasteners and 2 elastic leg strands and 2 elastic inter-leg gather strands. The backsheet was a white, breathable, nonwoven lamination. The entire diaper weighed 40 grams, with the fluff core weighing 12.6 g, the SAP weighing 10.9 g, the acquisition layer weighing 0.23 g. The entire diaper was 47 cm in length, 38 cm wide in the back, 28 cm wide in the front, and 23 cm at its narrowest point. The acquisition layer was 16 cm in length, 5 cm in width, resulting in a basis weight of 30 g/m². The fluff and SAP core was 40 cm in length, and a uniform 12 cm in width.

In sample 1, the diapers were used as is for the tests. In sample 2, the sides of the top sheet were cut along the side edge of the diaper, pulled back, replaced, and resealed with a hot air gun as a control for the diapers using particles. In sample 3, the sides of the top sheet were cut along the side edge of the diaper and the acquisition layer was removed. In examples 4-6 the sides of the top sheet were cut along the side edge of the diaper and the acquisition layer removed and replaced with particles of the type shown in the Table 2 in the amount shown in Table 2. In samples 3-6, the topsheet was replaced in the same manner as sample 2.

The diapers were tested for loaded acquisition times on an Anarewet Plus tester, obtained from Courtray Consulting, Douai, FRA. The basic operating procedure is as follows. Up to three diapers or test specimens are placed on top of a flat inflatable rubber bladder and a thick plastic plate is placed on top. The rubber bladder is inflated to the desired pressure. An aliquot of the desired fluid is automatically added to the insult point of the specimen and the time it takes to be fully absorbed into the diaper is electronically measured. After a specified pause, the insult procedure is repeated, followed by an additional pause and insult.

For both Examples 2 and 3 the insult point was 0.75 inches from the front edge of the acquisition patch. The front edge of this patch was approximately 5 inches from the front edge of the diaper. The pressure applied to the diaper was 10 mb. The volumes of the three insults were 60 ml each, and the pauses between the insults were 300 seconds. In this manner the loaded acquisition times were obtained and are listed in table 2.

TABLE 2

| Sample | Acquisition Layer | Weight of Particles or Acquisition Layer (g) | Loaded Acquisition Time (sec) | | | | | | | |
|---|---|---|---|---|---|---|---|---|---|---|
| | | | 1st Insult | | 2nd Insult | | 3rd Insult | | Total | |
| | | | ave | s.d | ave. | s.d | ave. | s.d | ave. | s.d. |
| 1 | As is | 0.23 | 17 | 1 | 39 | 6 | 64 | 11 | 119 | 17 |
| 2 | As is but opened | 0.23 | 20 | 3 | 43 | 7 | 68 | 13 | 130 | 22 |
| 3 | Removed | 0 | 22 | 1 | 50 | 4 | 85 | 9 | 158 | 14 |
| 4 | Particle 1 | 2.0 | 16 | 2 | 32 | 2 | 51 | 2 | 100 | 6 |
| 5 | Particle 1 | 0.5 | 22 | 3 | 47 | 11 | 76 | 19 | 144 | 33 |
| 6 | Particle 3 | 2.0 | 12 | 1 | 19 | 2 | 60 | 6 | 91 | 8 |

As show in the table, opening and reclosing the diaper increases the acquisition time slightly. This is a known phenomenon due to the disruption of the contact between the top sheet and the acquisition layer. The higher the level of contact there is, the faster the acquisition is. The table also shows that completely removing the acquisition layer raises the acquisition times substantially as expected. Replacing the acquisition layer with 2.0 gram of particle type 1, lowered the acquisition time by about 25% when compared to the control, "as is but opened" diaper. When the acquisition layer was replaced with only 0.5 g of particle 1, the acquisition time was slightly more than the "as is but opened" control diaper. When the acquisition layer was replaced with 2 grams of particle type 3, the double thick particle, the acquisition time drops about 30% when compared to the "as is but opened" control diaper. Because of the significantly higher basis weight of the particles compared to the high loft acquisition layer, a significantly higher total weight of particles had to be added to get a reasonable coverage, since each particle weighed on the order of 0.01-0.03 grams.

EXAMPLE 3

Example 3 illustrates another experiment run in an exactly same manner as Example 2 on the Anarewet tester. Table 3 shows the results of experiment.

TABLE 3

| Sample | Acquisition Layer | Weight of Particles or Acquisition Layer (g) | Number of Obs. | Loaded Acquisition Time (sec) | | | |
|---|---|---|---|---|---|---|---|
| | | | | 1st Insult ave. | 2$^{nd}$ Insult ave. | 3rd Insult ave. | Total ave. |
| 1 | As it but opened | 0.3 | 1 | 24 | 49 | 78 | 151 |
| 2 | Particle 2A | 2.2 | 1 | 15 | 30 | 46 | 91 |
| 3 | Particle 1A | 2.2 | 1 | 13 | 20 | 30 | 63 |
| 4 | Particle 5 | 2.2 | 1 | 8 | 9 | 12 | 29 |
| 5 | Particle 7A | 2.2 | 1 | 16 | 29 | 15 | 60 |
| 6 | Particle 6A | 2.2 | 1 | 13 | 19 | 25 | 57 |
| 7 | Particle 8 | 2.0 | 1 | 15 | 25 | 39 | 79 |

Samples 2-6 are all PET laminated particles of various shapes where particle 5 is also an adhesive laminated, double thick particle. Sample 1, the control, is reasonably close to the identical control in Example 2. Changes in ambient temperature and humidity can affect the acquisition time, and diapers do have a natural variability between them. The same trends appear in Example 3 as Example 2. Smaller circles and squares show an improvement with lower acquisition times than larger ones, and circles generally have a lower acquisition time than squares. When comparing PET laminated particles to non-laminated particles, one can see a sharp drop in the laminated particles acquisition time. For particle 1a, which is a laminated square, when compared to particle 1, which is the same square but not laminated, shows a 37% drop in total acquisition time. For particle 5, which is the laminated version of particle 3, an adhesive laminated double thick square, the drop is 73%.

While illustrative embodiments have been illustrated and described, it will be appreciated that various changes can be made therein without departing from the spirit and scope of the invention.

What is claimed is:

1. A cellulose pulp particle having the shape of a general prismatoid having two parallel bases, the pulp particle comprising hydrogen bonded cellulose pulp fibers in a wet laid pulp sheet form, one of the bases having an area that is equal to or greater than the area of the other base, the area of the larger base being equal to or less than 35 mm$^2$ and equal to or greater than 8 mm$^2$, and the height of the particle being equal to or greater than 0.9 mm and equal to or less than 6 mm, wherein the base of the particle has a dimension greater than the height of the particle, wherein the particle does not contain bulking fibers and wherein the particle has a basis weight of from 600 g/m$^2$ to 1000 g/m$^2$.

2. The particle of claim 1 in which the general prismatoid is a simple prismatoid.

3. The particle of claim 1 in which the general prismatoid is a cuboid.

4. The particle of claim 1 in which the general prismatoid is a square cuboid.

5. The particle of claim 1 in which the general prismatoid is a general cylinder.

6. The particle of claim 1 in which the general prismatoid is a right general cylinder.

7. The particle of claim 1 in which the general prismatoid is a right circular cylinder.

8. The particle of claim 1 in which the particle is formed from two or more plies, each of the plies comprising hydrogen bonded pulp fibers in a wet laid pulp sheet form, the adjacent plies being adhered together along a base, the height of the particle is equal to or greater than 1.5 mm and equal to or less than 6 mm and wherein each of the plies has a basis weight of from 600 $g/m^2$ to 1000 $g/m^2$.

9. The particle of claim 8 in which the general prismatoid is a simple prismatoid.

10. The particle of claim 8 in which the general prismatoid is a cuboid.

11. The particle of claim 8 in which the general prismatoid is a square cuboid.

12. The particle of claim 8 in which the general prismatoid is a general cylinder.

13. The particle of claim 8 in which the general prismatoid is a right general cylinder.

14. The particle of claim 8 in which the general prismatoid is a right circular cylinder.

\* \* \* \* \*